(12) United States Patent
Busoi et al.

(10) Patent No.: US 8,398,860 B2
(45) Date of Patent: Mar. 19, 2013

(54) METHOD OF PURIFYING A SURFACTANT BY ULTRAFILTRATION

(75) Inventors: Constantin Busoi, Bistrita (RO); Maria Rotaru, Bucharest (RO); Bogdan-Mihai Oghina, Bucharest (RO); Mariana Surmeian, Bucharest (RO)

(73) Assignee: Sindan Pharma SRL (RO)

( * ) Notice: Subject to any disclaimer, the term of this patent is extended or adjusted under 35 U.S.C. 154(b) by 745 days.

(21) Appl. No.: 11/884,213

(22) PCT Filed: Feb. 10, 2006

(86) PCT No.: PCT/EP2006/050856
§ 371 (c)(1),
(2), (4) Date: Aug. 1, 2008

(87) PCT Pub. No.: WO2006/084902
PCT Pub. Date: Aug. 17, 2006

(65) Prior Publication Data
US 2008/0287524 A1  Nov. 20, 2008

(30) Foreign Application Priority Data
Feb. 10, 2005  (RO) .................................. 200500092
Sep. 15, 2005  (EP) .................................... 05108513

(51) Int. Cl.
*B01D 61/00* (2006.01)
*A61K 31/337* (2006.01)

(52) U.S. Cl. ........ 210/651; 210/649; 210/634; 210/644; 210/653; 514/449

(58) Field of Classification Search ........................ None
See application file for complete search history.

(56) References Cited

U.S. PATENT DOCUMENTS

| | | | |
|---|---|---|---|
| 4,851,228 A * | 7/1989 | Zentner et al. | ................. 424/456 |
| 6,113,796 A | 9/2000 | Tounissou et al. | |
| 2004/0014624 A1 | 1/2004 | Bolkan et al. | |

FOREIGN PATENT DOCUMENTS

| | | |
|---|---|---|
| JP | 05 317654 | 12/1993 |
| JP | 09 110896 | 4/1997 |
| WO | WO 00/23070 | 4/2000 |
| WO | WO 01/72300 | 10/2001 |
| WO | WO 03/103714 | 12/2003 |

OTHER PUBLICATIONS

International Search Report from International Application No. PCT/EP2006/050856 dated Sep. 15, 2006.

\* cited by examiner

*Primary Examiner* — Yate K Cutliff
(74) *Attorney, Agent, or Firm* — Carter, DeLuca, Farrell & Schmidt, LLP

(57) ABSTRACT

A method of purifying a surfactant for use in a pharmaceutical formulation, which comprises mixing the surfactant with a solvent and bringing said mixture into contact with a semipermeable membrane so as to allow impurities present in the surfactant and having a molecular weight lower than the molecular weight cut-off of the membrane to pass through the membrane, whilst retaining the purified surfactant.

18 Claims, No Drawings

METHOD OF PURIFYING A SURFACTANT BY ULTRAFILTRATION

CROSS-REFERENCE TO RELATED APPLICATIONS

The present application claims the benefit of and priority to International Application No. PCT/EP2006/050856 filed on Feb. 10, 2006 claiming priority from each of Romanian Patent Application No. 200500092 filed on Feb. 10, 2005 and European Application No. 05108513.2 filed on Sep. 15, 2005, the entire contents of each of which are incorporated herein by reference.

The present invention relates to a method of purifying a surfactant. In particular, the present invention relates to a method of purifying a surfactant for use in a stabilized liquid pharmaceutical formulation, using a semi-permeable membrane filtration technique.

Poorly water-soluble pharmaceutically active agents can often present challenging formulation issues, especially if such drugs are to be administered in liquid form. Significant difficulties have been encountered, for example, with formulation of the potent antineoplastic agent paclitaxel, which is particularly insoluble in water. The structure of paclitaxel and some of its more important derivatives is shown below.

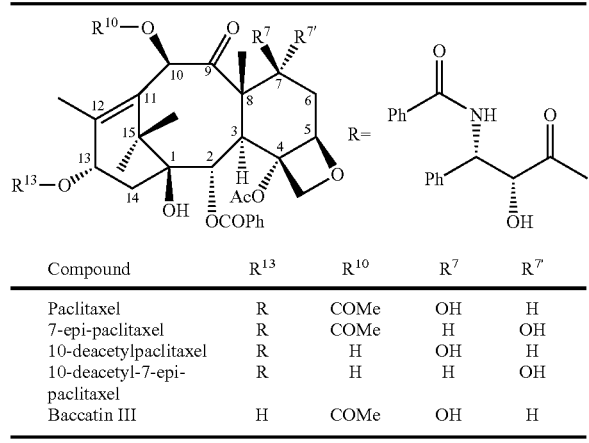

| Compound | $R^{13}$ | $R^{10}$ | $R^7$ | $R^{7'}$ |
|---|---|---|---|---|
| Paclitaxel | R | COMe | OH | H |
| 7-epi-paclitaxel | R | COMe | H | OH |
| 10-deacetylpaclitaxel | R | H | OH | H |
| 10-deacetyl-7-epi-paclitaxel | R | H | H | OH |
| Baccatin III | H | COMe | OH | H |

Taxol® is a commercially available paclitaxel formulation produced by Bristol-Meyers Squibb Company, 345 Park Avenue, New York, N.Y., USA 10154-0037. Taxol® contains paclitaxel in combination with a 50:50 mixture of dehydrated ethanol and Cremophor® EL (polyethoxylated caster oil available from BASF Aktiengesellschaft, Carl-Bosch-Straße 38, 67056 Ludwigshafen, Germany; other designations include European Pharmacopeia, 4$^{th}$ Edition, 2002: Castor oil, polyoxyl; United States Pharmacopeia—National Formulary: Polyoxyl 35 Castor Oil). Cremophor® EL is a non-ionic surfactant made by reacting castor oil with ethylene oxide in a molar ratio of 1:35. In Taxol®, Cremophor® EL is used as a drug delivery vehicle: after reconstitution for intravenous injection with a suitable fluid, such as physiologically acceptable saline or 5% dextrose solution, it forms large polar micelles to transport and deliver the entrapped drug to the target (see, for example, van Tellingen O. et al., *British Journal of Cancer* (1999) 81, 330-335).

Relatively high concentrations of Cremophor® EL are required to compensate for the insolubility of paclitaxel, and some patients have shown allergic reactions when administered such high concentrations of this surfactant. Moreover, certain fatty acid components of Cremophor® EL, particularly ricinoleic acid and octadecanoic acid, can lead to hepatotoxicity. To compound these problems, Cremophor® EL contains impurities which can catalyse the degradation of paclitaxel, the latter being susceptible in particular to mild basic hydrolysis; paclitaxel formulated with a mixture of dehydrated ethanol and commercial grade Cremophor® EL is therefore not sufficiently stable over time and has been shown to exhibit a loss of potency of greater than 60% after storage for 12 weeks at 50° C. (see, for example, EP 0,645,145). In view of these problems, various methods of purifying commercial grade Cremophor® EL have been investigated.

The main component of Cremophor® EL is glycerol polyethylene glycol ricinoleate, and this forms the hydrophobic part of the product together with fatty acid esters of polyethylene glycol; the smaller hydrophilic part consists of free polyethylene glycols and ethoxylated glycerol. Cremophor® EL forms clear solutions in water, and, in such aqueous solutions, it is stable towards electrolytes, e.g. acids and salts, provided that their concentration is not too high. Cremophor® EL has a molecular weight determined by steam osmometry of approximately 1630 (Fiedler, H. P., Lexicon der Hilfsstoffe fur Pharmazie, Kosmetik angrenzende Gebiete, Editio Cantor, 1989).

As paclitaxel is thought to be susceptible to mild basic hydrolysis, some investigations have focused on removing anionic carboxylate impurities in Cremophor® EL and/or controlling the pH of Cremophor® EL. WO 94/12031, for example, discloses that the stability of a composition comprising paclitaxel, Cremophor® EL and dehydrated ethanol can be improved by adding an acid to the composition to reduce its pH to the range 1 to 8, preferably 5 to 7. Powdered acids, especially citric acid, are preferred, but other acids such as acetic acid can also be used.

U.S. Pat. No. 5,925,776 discloses the treatment of Cremophor® EL by heating at around 50° C. to remove water, followed by addition of dehydrated alcohol and contact with a strong cationic exchange resin, particularly styrene divinyl benzene resin, which exchanges cations for H$^+$ ions. The pH of the solution is thereby reduced to lower than 4.2, and the solution can be used for the preparation of paclitaxel formulations.

WO 00/23070 discloses a method of contacting a solution of Cremophor® EL and dehydrated ethanol with an activated carbon column, to absorb water and unsaturated aliphatic and aromatic impurities. The solution is then contacted with a mixed bed ion exchange resin column, which replaces anions such as carboxylate anions with OH$^-$ and cations such as potassium ions with H$^+$. Residual water and ethanol is evaporated off, and the treated Cremophor® EL is redissolved in dehydrated ethanol and used to prepare a paclitaxel formulation. This formulation is shown to be more stable than one prepared with untreated Cremophor® EL.

EP 0,645,145 discloses that stabilized paclitaxel formulations can be obtained by adding acid to the Cremophor® EL used in their preparation, thereby neutralizing the carboxylate anions therein. The acid is preferably a mineral acid. Alternatively, Cremophor® EL can be contacted with aluminium oxide, for example in a chromatography column, to remove the carboxylate anions.

Other investigations have focused on the addition of a particular stabilising agent to Cremophor® EL. WO 01/72300, for example, discloses the treatment of Cremophor® EL with a non-toxic metal salt of an acid, such as zinc, copper or ferrous sulphate or gluconate, by heating them together or by passing the Cremophor® EL through a column containing the salt. Alternatively, chromatography has been used. The chromatographic purification of Cremophor® EL produces a less hepatotoxic drug vehicle (Oliver P. Flint et. al., 2001 American Society of Clinical Oncology Annual Meeting).

The purified version of Cremophor® EL available from BASF, Cremophor® ELP, was developed for sensitive pharmaceutical ingredients, and has a lower water to content, pH and viscosity, and also a reduced potassium ion and free fatty acid content, particularly with regard to ricinoleic, oleic and palmitic acids. Even Cremophor® ELP, however, does not provide an entirely satisfactory stability profile of paclitaxel formulations, and methods for further purifying this surfactant have been studied. For instance, WO 00/32186 discloses that a composition comprising paclitaxel and Cremophor® ELP can be stabilized by addition of an antioxidant such as sodium metabisulfite, sodium sulfite, sodium bisulfite, dextrose, a phenol, a thiophenol, or a combination thereof.

The method described in U.S. Pat. No. 5,925,776 is also disclosed to be applicable to the treatment of Cremophor® ELP. WO 03/103714, however, describes a disadvantage with the use of strong cationic exchange resins, such as those used in U.S. Pat. No. 5,925,776, that this can lead to a partial decomposition of the polyoxyethylated castor oil and an increased amount of free fatty acids. It states that the commercially available Cremophor® ELP has a lower content of basic compounds than Cremophor® EL, but still contains acidic impurities such as fatty acids and oxyethylated forms thereof, polyethyleneglycol diricinoleate and small amounts of corresponding free glycols. It discloses that treatment of Cremophor® ELP with an adsorbent such as silica gel or aluminosilicate can reduce the content of polar and acidic impurities, and paclitaxel formulations prepared with the treated Cremophor® ELP show a significantly lower degree of degradation into products such as 10-deacetylpaclitaxel and 7-epi-paclitaxel.

Despite these investigations, the factors influencing the decomposition of paclitaxel are still not fully understood.

All the above methods involve purification of a surfactant by chemical means, each with their own associated problems. For example, treatment with cationic resins or by addition of acids alters the pH of the surfactant away from physiological pH, which can be a disadvantage especially for injectable formulations. On the other hand, methods involving the addition of stabilizing chemicals carry the risk of introducing further toxic impurities contained in such chemicals. There is therefore a need in the art for a simple, mild but effective method of purifying a surfactant for use in a pharmaceutical formulation, particularly formulations comprising active agents that are sensitive to chemical reaction such as taxanes. The present invention solves this problem by purifying the surfactant using membrane filtration.

Membrane filtration is a technique widely used in the life sciences, most commonly for the separation, purification or concentration of proteins. Depending on membrane type it can be classified as microfiltration (membrane pore size between 0.1 and 10 µm) or ultrafiltration (membrane pore size between 0.001 and 0.1 µm). Ultrafiltration membranes are used for concentrating dissolved molecules (protein, peptides, nucleic acids, carbohydrates, and other biomolecules), desalting or exchanging buffers, and gross fractionation. An ultrafiltration membrane retains molecules that are larger than the pores of the membrane, while smaller molecules such as salts, solvents and water, which are 100% permeable, freely pass through the membrane. There are two main membrane filtration methods: in Single Pass/Dead End/Direct Flow Filtration (DFF), the fluid to be filtered is directed perpendicular to the membrane. In Cross Flow/Tangential Flow Filtration (TFF), the fluid flows tangential to the surface of the membrane; TFF solves the problem of membrane clogging by re-circulating the retentate.

In a first aspect of the invention, there is provided a method of purifying a surfactant for use in a pharmaceutical formulation, which comprises mixing the surfactant with a solvent and bringing said mixture into contact with a semi-permeable membrane so as to allow impurities present in the surfactant and having a molecular weight lower than the molecular weight cut-off of the membrane to pass through the membrane, whilst retaining purified surfactant.

In a second aspect of the invention, there is provided a purified surfactant obtainable by a method according to the invention in its first aspect.

In a third aspect of the invention, there is provided a solvent system comprising a purified surfactant according to the invention in its second aspect.

In a fourth aspect of the invention, there is provided a stabilized liquid formulation comprising a purified surfactant according to the invention in its second aspect.

In further aspects of the invention, there are provided pharmaceutical formulations comprising paclitaxel, dehydrated alcohol and glycerol polyethylene glycol ricinoleate, which contain:
less than 0.1% baccatine III;
less than 0.1% ethyl ester side chain of paclitaxel;
less than 0.1% 10-deactyl-paclitaxel;
less than 0.1% 10-deacetyl-7-epipaclitaxel; and/or
less than 0.2% 7-epipaclitaxel.

In a final aspect of the invention, there is provided a method of purifying a surfactant for use in a pharmaceutical formulation, which comprises forming a colloidal suspension of the surfactant in a solvent and subjecting the suspension to a physical separation technique, so as to remove impurities having a different molecular weight than that of the colloidal surfactant.

Preferred embodiments of the invention in any of its various aspects are as described below or as defined in the sub-claims.

When combined with a solvent, surfactants are capable of self-aggregating into numerous supramolecular structures including monolayers, bilayers and micelles having a wide variety of shapes. Such aggregates tend to exist in equilibrium with monomeric (i.e. non-aggregated) surfactant molecules. Micelles may be formed above a particular concentration of surfactant termed the critical micelle concentration; at this concentration there is a discontinuity in various physical properties such as surface tension, turbidity, molar conductivity and osmotic pressure. The critical micelle concentration can be affected by temperature and the presence of electrolytes; for example, micelles of ionic surfactants may only form above a particular temperature known as the Krafft temperature. Non-ionic surfactant solubility, however, has a temperature limit called the cloud point. These parameters are known for any particular surfactant or can be determined experimentally by known methods.

Micelles of a micellar solution tend to have an aggregation number (i.e. the number of aggregated surfactant molecules) around 20-100. In one embodiment of the invention, the surfactant forms micellar aggregates having an average molecular weight higher than the molecular weight cut-off of the membrane, which do not pass through the membrane during the filtration. Impurities present in the surfactant that have a molecular weight lower than the average molecular weight of the surfactant in its aggregated form can be separated by appropriate choice of the molecular weight cut-off of the membrane. The molecular weight of the surfactant in its monomeric form can be higher or lower than the molecular weight cut-off of the membrane. The invention is particularly useful for the removal of impurities having a molecular weight similar to or higher than that of monomeric surfactant, but lower than that of the surfactant micelles.

The solvent is preferably a polar solvent, in particular water. In one embodiment of the invention, the surfactant is mixed with water in a concentration of at least its critical micelle concentration before being subjected to membrane filtration, preferably TFF. The large micelles are retained, whereas smaller impurities in the colloidal suspension pass through the membrane. After the tangential flow filtration, water can be removed from the retentate by distillation at low pressure. Optionally, after the water removal, the surfactant is treated with activated charcoal or an ion exchange resin to reduce the coloration (absorbance at $\lambda=425$ nm) and improve the stability of the resultant pharmaceutical formulation. Preferably, the surfactant is treated with activated carbon with stirring for 30 minutes at room temperature, followed by filtration. Preferably, the surfactant is treated with the ion exchange resin with stirring for 30 minutes at room temperature, followed by filtration.

The surfactant may be of any type including ionic and non-ionic, but is preferably non-ionic. In one embodiment of the invention, the surfactant to be purified is a polyoxyl castor oil such as Cremophor® EL or ELP. Cremophor® EL or ELP forms large polar micelles in aqueous solutions, which will be retained by the membrane during filtration; the critical micelle concentration is approximately 0.02%. In contrast, smaller molecules, which can cause degradation of active agents such as paclitaxel, do not form micelles and will pass through the membrane. Such impurities may be ionic species, e.g. carboxylate anions or metal cations, or non-ionic species. The purified surfactant may also have a lower concentration of fatty acids than commercially available Cremophor® ELP.

Suitable conditions for the membrane filtration can be determined by the skilled person. For example, suitable flow rates may be in the range 30-100 ml/min, preferably 50-80 ml/min in respect of the retentate and 0.5-10 ml/min, preferably 0.5-5 ml/min, especially preferably 1-2 ml/min in respect of the filtrate. The membrane is preferably an ultrafiltration membrane; suitable molecular weight cut-offs may be in the range 2-20 kD, preferably 3-15 kD, especially preferably 5-10 kD. The filtration may be conducted under a pressure of 0.1-20 bars.

Although the invention has been described above in relation to the use of a membrane filtration technique, the skilled person will appreciate that similar physical separation techniques such as sucrose gradient centrifugation may be used in the alternative.

A suitable solvent system is needed to solubilise the active agent and ensure stability of the formulation, providing a sufficiently long shelf life. In addition, in the case of injectable formulations, these are often diluted prior to administration with a fluid, and the solvent system must be capable of maintaining the stability of the diluted form.

A potentially useful solvent system for this purpose would be a mixture of a pharmaceutically acceptable polar solvent, such as ethanol, and a surfactant. The surfactant in general acts as a solubiliser or emulsifier in the stabilised liquid formulation. Many useful surfactants are condensation products of an alkylene oxide, such as ethylene oxide, and a fatty acid or fatty alcohol. Polyoxyl castor oils and polysorbates (ethoxylated sorbitan esters), in particular, have been found to be of value in the invention. In appropriate cases, the surfactant may consist of a mixture of surfactant compounds.

The purified surfactants of the invention are particularly suitable for use in a wide range of stabilized liquid formulations comprising lipid-soluble drugs, especially injectable formulations. For instance, Cremophor® EL or ELP purified according to the invention can be used to prepare various solutions of numerous drugs including miconazole, hexedetine, clotrimazole and benzocaine, and also fat-soluble vitamins. Drugs that are particularly susceptible to degradation, such as paclitaxel, docetaxel, teniposide and camptothecin derivatives, are of major interest.

In embodiments of the invention, the pharmaceutical formulations comprising paclitaxel, dehydrated alcohol and glycerol polyethylene glycol ricinoleate contain:
  less than 0.06% baccatine III;
  less than 0.05% ethyl ester side chain of paclitaxel;
  less than 0.06% 10-deactyl-paclitaxel;
  no detectable 10-deacetyl-7-epipaclitaxel; and/or
  less than 0.16% 7-epipaclitaxel.

The following examples are intended to demonstrate the invention but are not intended to limit the claims in any manner.

EXAMPLE 1

80 g Cremophor® EL (BASF Aktiengesellschaft) were mixed with 400 g water for injection. The solution obtained was subjected to tangential flow filtration (TFF) using a Minimate® TFF System fitted with a 5 kD ultrafiltration membrane (Pall Corporation, 2200 Northern Boulevard, East Hills, N.Y. 11548, USA) for 48 hours at room temperature. The filtration pressure was between 2 and 3 bar. A water volume equal to the volume of filtrate was added to the retentate every hour. The total amount of water added to the retentate was approximately 4500 ml. The aqueous solution obtained was distilled at low pressure (500 µbar) on a water bath. 58 g of purified Cremophor® EL was obtained (Cremophor® EL-TFF-1).

The Cremophor® EL-TFF-1 was mixed with dehydrated ethanol and paclitaxel to obtain a pharmaceutical formulation (Formulation 1).
Formulation 1:

| Paclitaxel | 6 mg |
|---|---|
| Cremophor ® EL-TFF-1 | 527 mg |
| Dehydrated Ethanol | 49.7% v/v |

EXAMPLE 2

80 g Cremophor® ELP were mixed with 400 g water for injection. The solution obtained was subjected to TFF using a 5 kD membrane and a Minimate® TFF System from Pall for 40 hours at room temperature. The filtration pressure was between 2 and 3 bar. A water volume equal to the volume of filtrate was added to the retentate every hour. The total amount of water added to the retentate was approximately 4400 ml. The aqueous solution obtained was distilled at low pressure (500 µbar) on a water bath. 59 g of purified Cremophor® ELP was obtained (Cremophor® ELP-TFF-2).

The Cremophor® ELP-TFF-2 was mixed with dehydrated ethanol and paclitaxel to obtain a pharmaceutical formulation (Formulation 2).
Formulation 2:

| Paclitaxel | 6 mg |
|---|---|
| Cremophor ELP-TFF-2 | 527 mg |
| Dehydrated Ethanol | 49.7% v/v |

Comparative Example 1

A paclitaxel formulation containing commercial grade Cremophor® EL and dehydrated ethanol is prepared as follows (Formulation 3):

Formulation 3:

| | |
|---|---|
| Paclitaxel | 6 mg |
| Cremophor ® EL | 527 mg |
| Dehydrated Ethanol | 49.7% v/v |

Comparative Example 2

A paclitaxel formulation containing commercial grade Cremophor® ELP and dehydrated ethanol is prepared as follows (Formulation 4):

Formulation 4:

| | |
|---|---|
| Paclitaxel | 6 mg |
| Cremophor ® ELP | 527 mg |
| Dehydrated Ethanol | 49.7% v/v |

Comparative Example 3

A paclitaxel formulation containing commercial grade Cremophor® EL, dehydrated ethanol and citric acid is prepared as follows (Formulation 5):

Formulation 5:

| | |
|---|---|
| Paclitaxel | 6 mg |
| Cremophor ® EL | 527 mg |
| Citric acid (anhydrous) | 2 mg |
| Cremophor ® ELP-TFF-3 | 527 mg |
| Dehydrated Ethanol | 49.7% v/v |

Formulations 1-4 were subjected to an accelerated degradation study (36 hours at 56° C.) and tested for the presence of the following degradation products: baccatineIII, ethyl ester side chain, 10-deacetylpaclitaxel, 10-deacetyl-7-epi-paclitaxel and 7-epi-paclitaxel. The results are presented in Table 1.

TABLE 1

| | Formulation 1 EL-TFF-1 | Formulation 2 ELP-TFF-2 | Formulation 3 Cremophor ® EL | Formulation 4 Cremophor ® ELP |
|---|---|---|---|---|
| Baccatine III (%) | 0.52 | 0.06 | 4.65 | 0.42 |
| Ethyl ester side chain (%) | 0.41 | 0.05 | 3.68 | 0.34 |
| 10-Deacetyl-paclitaxel (%) | 0.07 | 0.03 | 0.28 | 0.02 |
| 10-Deacetyl-7-epi-paclitaxel (%) | ND | ND | 0.06 | ND |
| 7-epipaclitaxel (%) | 0.41 | 0.16 | 2.97 | 0.27 |

ND = not detected

The stability of Formulation 2 in 0.9% NaCl perfusable solution (1.2 mg/ml paclitaxel/ml diluted solution) was tested and compared with the stability in the same conditions of the product Taxol® and Formulation 5. The paclitaxel assay was comparable for Formulation 2, Taxol® and Formulation 5 (Table 2). The turbidity of the solution prepared with Formulation 2 was lower than the turbidity of the perfusable solutions obtained with Taxol® and Formulation 5 (Table 3).

TABLE 2

| | Paclitazel Assay (%) | | |
|---|---|---|---|
| | Initially | 24 h | 27 h |
| Formulation 2 (ELP-TFF-2) | 100 | 100.4 | 99.35 |
| Taxol ® | 100 | 98.33 | 98.59 |
| Formulation 5 (with citric acid) | 100 | 99.09 | 100.91 |

TABLE 3

| | Turbidity (NTU) | | | | |
|---|---|---|---|---|---|
| | Initially | 12 h | 24 h | 27 h | 40 h |
| Formulation 2 (ELP-TFF-2) | 4.39 | 4.36 | 4.31 | 4.24 | 4.63 |
| Taxol ® | 4.72 | 5.12 | 5.33 | 5.41 | 5.22 |
| Formulation 5 (with citric acid) | 4.44 | 4.67 | 4.12 | 4.93 | 5.12 |

EXAMPLE 3

80 g Cremophor® ELP were mixed with 400 g water for injection. The solution obtained was subjected to TFF using a 10 kD membrane and a Minimate® TFF System from Pall for 30 hours at room temperature. The filtration pressure was between 2 and 3 bar. A water volume equal to the volume of filtrate was added to the retentate every hour. The total amount of water added to the retentate was approximately 3200 ml. The aqueous solution obtained was distilled at low pressure (500 µbar) on a water bath. 70 g of purified Cremophor® ELP was obtained (Cremophor® ELP-TFF-3).

Purified Cremophor® ELP-TFF-3 (15 g) was mixed with dehydrated ethanol and paclitaxel to obtain a pharmaceutical formulation (Formulation 6).

Formulation 6:

| | |
|---|---|
| Pacitaxel | 6 mg |
| Cremophor ° ELP-TFF-3 | 527 mg |
| Dehydrated Ethanol | 49.7% v/v |

Purified Cremophor® ELP-TFF-3 (15 g) was mixed with dehydrated ethanol (1/1 v/v). The solvent mixture was treated with activated carbon (Merck) with stirring for 30 minutes at room temperature, followed by filtration. The charcoal treated solvent was added to paclitaxel to obtain a pharmaceutical formulation (Formulation 7).

Formulation 7:

| | |
|---|---|
| Paclitaxel | 6 mg |
| Charcoal treated solvent (Cremophor ® ELP-TFF-3/ Dehydrated Ethanol) | Up to 1 ml |

Purified Cremophor® ELP-TFF-3 (15 g) was mixed with dehydrated ethanol (1/1 v/v). The solvent mixture was treated with the weak cationic exchange resin Purolite C106EP with stirring for 30 minutes at room temperature, followed by filtration. The resin-treated solvent was added to paclitaxel to obtain a pharmaceutical formulation (Formulation 8).
Formulation 8:

| Paclitaxel | 6 mg |
|---|---|
| Resin treated solvent (Cremophor ® ELP-TFF-3/ Dehydrated Ethanol) | Up to 1 ml |

Formulations 4 and 6-8 were subjected to an accelerated degradation study (7 days at 56° C.) and tested for the presence of the following degradation products: baccatine III, ethyl ester side chain, 10-deacetylpaclitaxel, 10-deacetyl-7-epi-paclitaxel and 7-epi-paclitaxel. The results are presented in Table 4.

TABLE 4

|  | Formulation 6 | Formulation 7 | Formulation 8 | Formulation 4 |
|---|---|---|---|---|
| Baccatine III % | 0.08 | 0.07 | 0.02 | 0.69 |
| Ethyl ester side chain % | 0.06 | 0.05 | 0.03 | 0.49 |
| 10-Deacetylpaclitaxel % | 0.13 | 0.27 | 0.29 | 0.23 |
| 10-Deacetyl-7-epi-paclitaxel % | ND | ND | ND | ND |
| 7-epipaclitaxel % | 0.33 | 0.19 | 0.17 | 0.47 |

ND = Not Detected

The results of the accelerated degradation study at 56° C. and the stability tests in perfusable solutions showed that the polyoxyl castor oil purified according to this invention is suitable for the preparation of stabilized formulations containing paclitaxel.

The invention claimed is:

1. A method of treating a surfactant for use in a stabilized liquid pharmaceutical formulation of a lipid soluble drug for injection, the surfactant being a condensation product of castor oil and ethylene oxide and the lipid-soluble drug being susceptible to degradation in the presence of the surfactant in untreated form, which comprises:
    mixing the surfactant with a solvent to form a mixture;
    bringing said mixture into contact with a semi-permeable membrane so as to allow impurities present in the surfactant and having a molecular weight lower than the molecular weight cut-off of the membrane to pass through the membrane, wherein the mixture flows tangential to a surface of the semi-permeable membrane and purified surfactant is retained; and
    distilling the purified surfactant at a low pressure.

2. A method as claimed in claim 1, wherein the surfactant forms one or more aggregates in the mixture.

3. A method as claimed in claim 1, where the surfactant is present in the solvent in the form of a colloidal dispersion or suspension.

4. A method as claimed in claim 1, wherein the surfactant is present in the mixture at a concentration of at least its critical micelle concentration.

5. A method as claimed in claim 1, wherein the mixture contains surfactant in the form of micelles having an average molecular weight higher than the molecular weight cut-off of the semi-permeable membrane.

6. A method as claimed in claim 5, wherein at least one impurity has a molecular weight that is lower than the average molecular weight of the micelles.

7. A method as claimed in claim 1, wherein at least one impurity has a molecular weight that is higher than that of the surfactant when the surfactant is not present in admixture with the solvent.

8. A method as claimed in claim 1, wherein the surfactant, in the absence of the solvent, has a molecular weight lower than the molecular weight cut-off of the semi-permeable membrane.

9. A method as claimed in claim 1, wherein the mixture is an aqueous mixture.

10. A method as claimed in claim 1, wherein the surfactant is a non-ionic surfactant.

11. A method as claimed in claim 1, wherein the surfactant is derived from a vegetable oil.

12. A method as claimed in claim 1, wherein the semi-permeable membrane is an ultra-filtration membrane.

13. A method of treating a surfactant for use in a stabilized liquid pharmaceutical formulation of a lipid soluble drug for injection, wherein the surfactant is a condensation product of castor oil and ethylene oxide and the lipid-soluble drug is susceptible to degradation in the presence of the surfactant in untreated form, which comprises:
    forming a colloidal suspension of the surfactant in a solvent;
    subjecting the colloidal suspension to tangential flow filtration, so as to remove impurities having a different molecular weight than that of the colloidal surfactant and obtain purified surfactant; and
    distilling the purified surfactant at a low pressure.

14. A method as claimed in claim 13, wherein the surfactant is derived from a vegetable oil.

15. A method as claimed in claim 12, wherein the ultra-filtration membrane-comprises a molecular weight cut-off in the range from about 2 to about 20 kD.

16. A method as claimed in claim 1, further comprising:
    combining the distilled purified surfactant with a lipid-soluble drug being susceptible to degradation in the presence of the surfactant in an untreated form.

17. A method as claimed in claim 16, wherein the drug comprises paclitaxel, docetaxel or teniposide.

18. A method as claimed in claim 16, wherein the drug comprises paclitaxel.

* * * * *